United States Patent [19]

Distler et al.

[11] Patent Number: 4,478,759
[45] Date of Patent: Oct. 23, 1984

[54] PREPARATION OF AMINOITRILES

[75] Inventors: Harry Distler, Bobenheim; Karl-Ludwig Hock, Ludwigshafen, both of Fed. Rep. of Germany

[73] Assignee: BASF Aktiengesellschaft, Fed. Rep. of Germany

[21] Appl. No.: 283,649

[22] Filed: Jul. 15, 1981

[30] Foreign Application Priority Data

Aug. 1, 1980 [DE] Fed. Rep. of Germany ....... 3029205

[51] Int. Cl.$^3$ .................. C07C 120/00; C07C 120/43
[52] U.S. Cl. .............................................. 260/465.5 A
[58] Field of Search ................. 260/465.5 A

[56] References Cited

U.S. PATENT DOCUMENTS

| | | | |
|---|---|---|---|
| 2,855,428 | 10/1958 | Singer et al. | 260/465.5 A |
| 3,061,628 | 10/1962 | Singer, Jr. et al. | 260/465.5 A |
| 3,337,607 | 8/1967 | Wollensak | 260/465.5 A |
| 3,504,011 | 3/1970 | Gandhi | 260/465.5 A |
| 3,925,448 | 12/1975 | Lanier | 260/465.5 A |
| 3,959,342 | 5/1976 | Homberg et al. | 260/465.5 A |
| 3,984,453 | 10/1976 | Chaberey | 260/465.5 A |
| 4,022,815 | 5/1977 | Schlecht et al. | 260/465.5 A |
| 4,113,764 | 9/1978 | Distler et al. | 260/465.5 A |
| 4,134,889 | 1/1979 | Distler et al. | 260/465.5 A |

FOREIGN PATENT DOCUMENTS

| | | | |
|---|---|---|---|
| 1493910 | 12/1969 | Fed. Rep. of Germany | 260/465.5 A |
| 1768257 | 3/1972 | Fed. Rep. of Germany | |
| 2503582 | 8/1976 | Fed. Rep. of Germany | |

OTHER PUBLICATIONS

Ullmanns Encyklopadie d. Techn. Chemie, 4th ed., vol. 8, pp. 198–199, vol. 17, pp. 339–941.

Primary Examiner—Joseph P. Brust
Attorney, Agent, or Firm—Keil & Weinkauf

[57] ABSTRACT

Aminonitriles are prepared by reacting a nitrogen compound with formaldehyde and hydrogen cyanide in the presence of an additional acid at a pH below 2 and at from 10° to 70° C., the concentration of the hydrogen cyanide during the reaction being not more than 3 per cent by weight, based on the reaction mixture.

The aminoacetonitriles obtained by the novel process are valuable starting materials for the preparation of dyes, fungicides, bactericides, textile assistants, rubber additives, and auxiliaries used in water softening, cosmetics, the photographic industry, the paper industry and the electroplating industry.

9 Claims, No Drawings

PREPARATION OF AMINOITRILES

The present invention relates to a process for the preparation of aminonitriles by reacting a nitrogen compound with formaldehyde and hydrogen cyanide in the presence of an additional acid at a pH below 2 and at from 10° to 70° C., the concentration of the hydrogen cyanide during the reaction being not more than 3 percent by weight, based on the reaction mixture.

It is known from German Published Application DAS 1,493,910, U.S. Pat. Nos. 2,855,428 and 3,959,342 that ammonia, hydrogen cyanide and formaldehyde can undergo an exothermic reaction, in the presence or absence of an added acid, at an elevated temperature, for example at from 40° to 60° C., to give nitrilotriacetonitrile. The overall yield in these rapid exothermic reactions is unsatisfactory; even lowering the reaction temperature only slightly diminishes the formation of undesired by-products, whilst on the other hand necessitating an increase in reaction time and hence entailing a reduction in the space-time yield. A similar process is disclosed in U.S. Pat. No. 3,984,453.

The hydrogen cyanide concentration during the reaction is 10–20.3 percent by weight according to Example 1 of German Published Application DAS No. 1,493,910, from 10 to 30.7 percent by weight according to the Examples of U.S. Pat. No. 2,855,428 and from 7 to 12 percent by weight according to the Examples of U.S. Pat. No. 3,959,342, the percentages in each case being based on the reaction mixture.

German Laid-Open Application DOS No. 1,768,257 discloses a two-stage process, intended to overcome these difficulties, in which first a mixture of ammonia, hydrogen cyanide and formaldehyde is reacted in an acidic, aqueous medium at from about 0° to 45° C. to give a reaction mixture, containing methylene-bis-iminodiacetonitrile as an intermediate, after which the mixture containing the intermediate is heated at from about 45° to 120° C. The pH of the reaction mixture is intended to be below 3. The molar ratio of ammonia:hydrogen cyanide:formaldehyde in the starting mixture is generally from about 1:3:3 to about 1:4:4. The Examples show that the hydrogen cyanide concentration from the beginning, and during the first stage carried out at from 0° to 45° C., is not less than 7 percent by weight, and in general from 7 to 20 percent by weight, whilst in the second stage of the reaction, at from 45° to 120° C., it is not less than 7, and in general from 7 to 15, percent by weight, based on the reaction mixture. In spite of an involved 2-stage process, the yield and purity of the nitrilotriacetonitrile obtained are unsatisfactory.

The high standards of purity which are nowadays required of aminoacetic acids, in particular of nitrilotriacetic acid, ie. of the hydrolysis products of the compounds I for use in the detergent sector necessitate that the products I should themselves be very pure; in particular, their purity as determined by gas chromatography should be not less than 99%, and, specifically, the content of iminodiacetic acid should be not nore than 0.2%. In the conventional one-stage processes, the product is often found to contain impurities, for example, in the case of aminotriacetonitrile, from 0.2 to 2 percent by weight of iminodiacetonitrile, from 0.1 to 2 percent by weight of methylene-bis-amino compounds, from 0.01 to 0.1 percent by weight of cyanohydrin, from 0.01 to 0.1 percent by weight of polyoxymethylenes, from 0.1 to 1 percent by weight of α-aminomonoacetonitrile and from 0.1 to 0.2 percent by weight of other by-products, all these percentages being based on aminotriacetonitrile. Using the two-stage process described above, the impurities found in aminotriacetonitrile are as a rule from 0.2 to 0.8 percent by weight of iminodiacetonitrile, from 0.2 to 0.5 percent by weight of methylene-bis-amino compounds, from 0.1 to 0.2 percent by weight of cyanohydrin, from 0.01 to 0.1 percent by weight of polyoxymethylenes, from 0.1 to 0.2 percent by weight of α-aminomonoacetonitrile and about 0.2 percent by weight of other by-products, the percentages each being based on aminotriacetonitrile. Since methylene-bis-iminodiacetonitrile is obtained in a crystalline form and must be further reacted in the solid form, ie. in a type of topochemical reaction, with hydrogen cyanide and formaldehyde to give nitrilotriacetonitrile, it is not possible to prevent the presence of impurities in the end product.

German Pat. No. 2,503,582 discloses that N-alkyl-glycinonitriles are obtained by reacting formaldehyde with a primary or secondary N-alkylamine and hydrogen cyanide in the presence of water for from 0.1 to 4 hours at from 0° to 40° C., the concentration of hydrogen cyanide during the reaction being not more than 0.1 percent by weight, based on the reaction mixture.

We have found that aminoacetonitriles of the formula

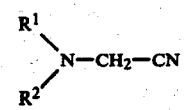

I where $R^1$ and $R^2$ may be identical or different and each is —CH$_2$—CN or

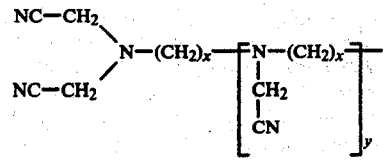

$R^1$ can also be an aliphatic hydrocarbon radical, x and y can be identical or different and each is an integer, and y can also be 0, are obtained in an advantageous manner by reacting ammonia or an amine with formaldehyde and hydrogen cyanide in the presence of another acid, if the nitrogen compound used has the formula

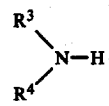

II where $R^3$ and $R^4$ are each hydrogen, or $R^3$ and/or $R^4$ are

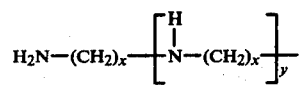

if $R^1$ and/or $R^2$ are

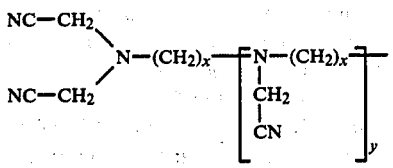

and $R^3$ can also have the same meaning as $R^1$ if $R^1$ is an aliphatic radical, and x and y have the above meanings, at a pH of below 2, and at from 10° to 70° C., the concentration of hydrogen cyanide during the reaction being not more than 3 percent by weight, based on the reaction mixture.

Where ammonia is used the reaction can be represented by the following equation:

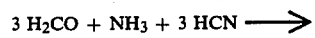

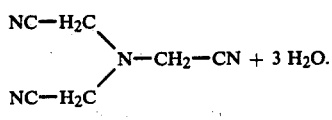

Compared to the conventional processes, the process according to the invention gives aminoacetonitriles more simply and more economically, in better yield and higher purity. The process is particularly suitable for industrial use and for continuous operation, presents no significant effluent problems and is ecologically more advantageous than the conventional processes. The by-products generally found are less than 0.2 percent by weight of iminodiacetonitrile, less than 0.001 percent by weight of methylene-bis-amino compounds, less than 0.001 percent by weight of cyanohydrin, less than 0.001 percent by weight of polyoxymethylenes and less than 0.001 percent by weight of α-aminomonoacetonitrile, the percentages each being based on aminotriacetonitrile, and a similar reduced formation of by-products is found in the case of all the other aminoacetonitriles. All these advantageous properties are surprising in view of the prior art. The low reaction temperature, and the low hydrogen cyanide concentration relative to the nitrogen compound II, at the start and during the reaction, would specifically have been expected to result in increased formation of methylene-bis-amino compounds, a longer reaction time and correspondingly greater decomposition and formation of heterogeneous products. In view of German Pat. No. 2,503,582, it is in particular surprising that larger amounts of α-aminomonoacetonitrile and α-iminodiacetonitrile by-products are not formed.

Formaldehyde can be used in liquid form or as a gas, and is in general used in the form of an aqueous solution, advantageously of from 10 to 50 percent strength by weight, preferably of from 30 to 40 percent strength by weight. Hydrogen cyanide can be used as a gas or, advantageously, as a liquid. The starting material II can be used undiluted or, advantageously, in solution, preferably in aqueous solution; the strength of the solution is advantageously from 40 to 60 percent by weight. Ammonia is preferably employed as a formaldehyde adduct, for example hexamethylenetetramine, formed by mixing the components at room temperature. This has the advantage that substantially less acid, for example from half to one-third of the stoichiometric amount of sulfuric acid, is required to neutralize the ammonia, and accordingly less salt load is created in the waste liquors obtained in due course.

The three starting materials can be employed in stoichiometric amounts, or any one of the components can be employed in excess, the preferred amounts being from 1 to 1.1 moles of starting material II and/or from 1 to 1.1 moles of hydrogen cyanide per mole of 100% formaldehyde.

Preferred starting materials II and accordingly preferred end products I are those where $R^3$ and $R^4$ are identical or different and each is hydrogen, $R^3$ and/or $R^4$ can also be

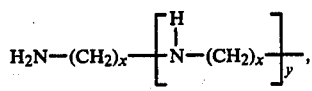

if $R^1$ and/or $R^2$ is

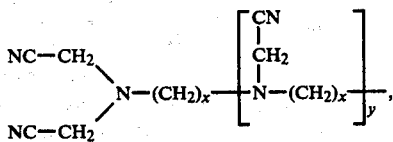

$R^1$ and $R^2$ can be identical or different and each can be —$CH_2$—CN or

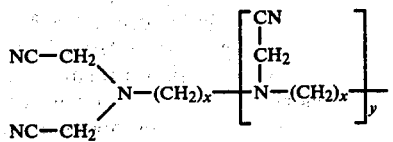

and $R^3$ and $R^1$ can also each be alkyl of 1 to 8, especially of 1 to 4, carbon atoms, and the symbols x and y can be identical or different, and x is 1 or 3 or preferably 2 and y is 3 or 2 or preferably 0 or 1. The above radicals can additionally be substituted by groups which are inert under the reaction conditions, for example alkyl or alkoxy, each of 1 to 4 carbon atoms. If y is 0, x is advantageously 2 or 3.

Examples of suitable starting materials II are ammonia, methylamine, ethylamine, n-propylamine, isopropylamine, n-butylamine, isobutylamine, sec.-butylamine, tert.-butylamine, pentylamine, pentyl-2-amine, pentyl-3-amine, n-hexylamine, n-heptylamine, n-octylamine, n-nonylamine, n-decylamine and 2-ethylhexylamine; ethylenediamine, propylenediamine, isopropylenediamine, butylenediamine, sec.-butylenediamine, isobutylenediamine and tert.-butylenediamine; diethylenetriamine, dipropylenetriamine, diisopropylenetriamine, dibutylenetriamine, diisobutylenetriamine, di-sec.-butylenetriamine and ditert.-butylenetriamine; triethylenetetramine, tripropylenetetramine, triisopropylenetetramine, tributylenetetramine, tri-sec.-butylenetetramine, triisobutylenetetramine and tri-tert.-butylenetetramine; tetraethylenepentamine, tetrapropylenepentamine, tetraisopropylenepentamine, tetrabutylenepentamine, tetraisobutylenepentamine, tetrasec.-butylenepentamine and tetra-tert.-butylenepentamine; nitrilo-(triethyleneamine), nitrilo-(tripropyleneamine), nitrilo-(triisopropyleneamine), nitrilo-(tributyleneamine), nitrilo(triisobutyleneamine), nitrilo- (tri-sec.-butyleneamine) and nitrilo-(tri-tert.-butyleneamine).

The reaction is carried out at from 0° to 70° C., advantageously from 10° to 60° C., preferably from 15° to 55° C., especially from 20° to 49° C., under reduced pressure, atmospheric pressure or superatmospheric pressure, batchwise or, preferably, continuously. As a rule, the reaction is carried out in the presence of water, advantageously introduced as an aqueous formaldehyde solution and/or aqueous acid solution; furthermore, water forms in the reaction itself. A suitable total amount of water is from 40 to 80, preferably from 70 to 60, percent by weight, based on formaldehyde. Hydrogen cyanide is added to the starting mixture before and during the reaction, in such amount that its concentration, based on reaction mixture, during the reaction does not exceed 3 percent by weight and is suitably from 0.01 to 3, advantageously from 0.01 to 2, preferably from 0.01 to 1, especially from 0.05 to 1, and very particularly from 0.05 to 0.7, percent by weight. The reaction time (or, in continuous operation, the residence time) is advantageously from 0.1 to 12, preferably from 1 to 6, hours. Preferably, water is used as the sole solvent, but organic solvents which are inert under the reaction conditions can also be present. Examples of such solvents are aromatic hydrocarbons, for example toluene, benzene, ethylbenzene, o-, m- and p-xylene, isopropylbenzene and methylnaphthalene; aliphatic and cycloaliphatic hydrocarbons, for example heptane, α-pinene, pinane, nonane, o-, m- and p-cymene, gasoline fractions boiling within a range of from 70° to 190° C., cyclohexane, methylcyclohexane, petroleum ether, decalin, hexane, naphtha, 2,2,4-trimethylpentane, 2,2,3-trimethylpentane, 2,3,3-trimethylpentane and octane; and mixtures of these. The solvent is advantageously used in an amount of from 40 to 10,000 percent by weight, preferably from 50 to 1,500 percent by weight, based on starting material II.

The reaction is carried out at a pH below 2, advantageously of from 0.1 to 2, preferably from 0.1 to 1. A strong acid is used as the additional acid, and for adjusting the pH. For the purposes of the invention, a strong acid is an organic or inorganic acid which is inert under the reaction conditions and has a pKa of from −7 to +2.16; a definition of the pKa is given in Ullmanns Encyklopädie der technischen Chemie, Volume 15, page 2. Examples of suitable acids are concentrated sulfuric acid, advantageously of 90°–98 percent strength by weight; phosphoric acid, advantageously of 70–90 percent strength by weight; hydrochloric acid, advantageously of 10–35 percent strength by weight; nitric acid, advantageously of 10–30 percent strength by weight; perchloric acid, advantageously of 10–40 percent strength by weight; and formic acid, advantageously of 10–90 percent strength by weight. Other acids which can be used are hydrogen chloride gas, boric acid, sulfonic acids, eg. benzenesulfonic acid and p-toluenesulfonic acid trichloroacetic acid and strongly acidic ion exchangers. Preferred acids are concentrated hydrochloric acid, concentrated sulfuric acid or phosphoric acid, especially of the concentrations mentioned for these acids above. The amount of acid used is advantageously from 0.5 to 1.5, preferably from 0.5 to 1, parts by weight (or an equivalent amount, in the case of an acidic ion exchanger) per part by weight of starting material II.

The reaction can be carried out as follows: a mixture of formaldehyde, water, hydrogen cyanide, added acid and starting material II, with or without an organic solvent, is kept at the reaction temperature. Some of the hydrogen cyanide is added to the starting mixture, and the remainder is added during the reaction, in portions or continuously, at a rate such that the hydrogen cyanide concentration mentioned above is maintained throughout the reaction time. The hydrogen cyanide concentration is advantageously measured continuously by means of a silver/calomel electrode. Finally, the end product is isolated from the reaction mixture in a conventional manner, for example by distillation or filtration.

The hydrolysis of the end product I is carried out in accordance with conventional methods, as a rule in an alkaline medium, preferably in an aqueous solution of an alkaline earth metal hydroxide or alkali metal hydroxide or, advantageously, of an alkali metal salt such as sodium or potassium carbonate, bicarbonate, acetate or formate. Sodium hydroxide and potassium hydroxide are especially preferred. For example, 30–40 percent strength by weight mixtures of the end product I are employed in such solutions and the hydrolysis is advantageously carried out at a pH of from 9 to 14 and at from 30° to 100° C. for from 2 to 30 hours. For example, the alkali, alkali metal salt or aqueous solution of these is added to the reaction mixture and the end product I in the mixture is hydrolyzed in the above manner. Advantageously, the hydrolysis is carried out with from 1 to 2 equivalents of alkali or alkali metal salt if the isolated end product I is used and from 1 to 6 equivalents of alkali or alkali metal salt if the non-isolated end product I, contained in the reaction mixture as mentioned above, is used. In an advantageous embodiment, the reaction mixture passes through a plurality of hydrolysis stages, preferably 2 or 3, at increasing temperatures, for example through a stirred kettle cascade with the kettles at 30°–40° C., 60° C. and 100° C. The hydrolysis is preferably carried out under reduced pressure, advantageously from 200 to 800 mbar, especially from 400 to 600 mbar. This stepwise hydrolysis under reduced pressure surprisingly prevents discolorations and decreases in yield. The salt of the aminoacetic acid corresponding to the end product I is finally isolated from the hydrolysis mixture in a conventional manner, for example by evaporation, crystallization and filtration.

The aminoacetonitriles obtained by the novel process are valuable starting materials for the preparation of dyes, fungicides, bactericides, textile assistants, rubber additives, and auxiliaries used in water softening, cosmetics, the photographic industry, the paper industry and the electroplating industry. Regarding their use, reference may be made to the above publications and to Ullmanns Encyklopädie der technischen Chemie, (4th edition), Volume 8, pages 198 and 199, and Volume 17, pages 339–341.

In the Examples which follow, parts are by weight.

EXAMPLE 1

Per hour, 70 parts of hexamethylenetetramine, 300 parts of aqueous 30 percent strength by weight formaldehyde, 162 parts of liquid hydrogen cyanide and 150 parts of 63 percent strength by weight sulfuric acid are introduced, from separate feed vessels, into a reactor, and are reacted at 45° C. During the reaction, the hydrogen cyanide concentration does not exceed 1 percent by weight, based on total mixture, and averages from 0.5 to 0.9 percent by weight. During the reaction, the pH is <1 and the reaction temperature 45° C. The residence time is 6 hours. The reaction mixture is finally cooled and filtered. Per hour, 255.8 parts of nitrilotriacetonitrile (95.46% of theory) are obtained; the product melts at 127.5°-128.5° C. and has a purity, according to gas chromatography, of >99.8 percent.

EXAMPLE 2

(a) 240 parts of ethylenediamine and 823 parts of 55 percent strength by weight sulfuric acid are mixed in a stirred vessel at 20° C., with external cooling. The mixture is dissolved in 800 parts of water.

With the pH at <1 and the temperature at 44° C., 1,600 parts of aqueous 37 percent strength by weight formaldehyde and 432 parts of liquid hydrogen cyanide are added simultaneously at a rate such that the hydrogen cyanide concentration during the reaction does not exceed one percent by weight, based on total mixture. The residence time in the reactor is 6 hours. The hydrogen cyanide concentration averages 0.5 to 1 percent by weight, based on total mixture. During the reaction, the pH is <1 and the reaction temperature is 44° C. The reaction mixture is finally cooled and filtered.

823 parts (95% of theory) of ethylenediaminetetraacetonitrile are obtained as colorless crystals of melting point 131°-132° C. The purity, according to gas chromatography, is >99.8 percent.

(b) Use 108 parts of ethylenediaminotetraacetonitrile, 200 parts of water and 273 parts of 30 percent strength by weight aqueous NaOH are introduced into a stirred vessel and reacted for 9 minutes under 400 mbar. Using a residence time of 60 minutes for final reaction at 60° C., complete solution occurs. The mixture is then heated in the course of 30 minutes to 100° C. under 400 mbar, whilst at the same time introducing steam. After a residence time of one hour at 100° C., the hydrolysis is complete. 465 parts of an almost colorless solution (APHA=60-80) are obtained.

EXAMPLE 3

337 parts of diethylenetriamine and 400 parts of water at 20° C. are introduced into a stirred vessel. 900 parts of 55 percent strength by weight sulfuric acid are then introduced into the clear, colorless solution at 20° C., whilst cooling and stirring. 1,500 parts of aqueous 30 percent strength by weight formaldehyde and 405 parts of liquid hydrogen cyanide are then added slowly at a pH of <1 and at 16° C., at a rate such that during the reaction the hydrogen cyanide concentration does not exceed 2 percent by weight, based on total mixture. The residence time in the reactor is 2 hours. The hydrogen cyanide concentration varies from 0.5 to 1 percent by weight, based on total mixture. During the reaction, the pH is <1 and the temperature 48° C. The mixture is then cooled and filtered. 889 parts (99.4% of theory) of diethylenetriaminopentaacetonitrile, of melting point 104°-105° C., are obtained. Purity, according to gas chromatography, >99.8 percent by weight.

EXAMPLE 4 (COMPARATIVE EXAMPLE)

450 parts of 37 percent strength aqueous formaldehyde (5.55 moles) and 132 parts of ammonium sulfate (2 moles of $NH_4^\oplus$) are heated in a stirred kettle, and a mixture of 500 parts of water, 30.6 parts of concentrated sulfuric acid and 167.4 parts of hydrogen cyanide is introduced in the course of 15 minutes, from a feed vessel which can be cooled. After this addition, the pH is 0.51 and the temperature rises to about 70° C., with refluxing of hydrogen cyanide. During the reaction, the hydrogen cyanide concentration is 4.56 percent. The reaction mixture is cooled to 25° C. and the solid is filtered off and dried at 80° C. Nitrilotriacetonitrile, of melting point 127.5° C., is obtained in a yield of 66.42% of theory; its purity, according to gas chromatography, is 96.4 percent.

We claim:

1. A process for the preparation of an aminoacetonitrile of the formula

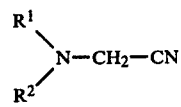

where $R^1$ and $R^2$ may be identical or different and each is $-CH_2-CN$ or

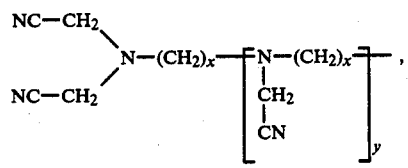

$R^1$ can also be an alkyl of 1 to 8 carbon atoms and the symbols X and Y can be identical or different and x is 1, 2 or 3 and y is 0, 1, 2 or 3, which process comprises: reacting ammonia or an amine with formaldehyde and hydrogen cyanide in the presence of an additional acid, wherein the nitrogen compound used has the formula

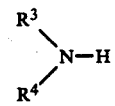

where $R^3$ and $R^4$ are each hydrogen, or $R^3$ or $R^4$ or both are

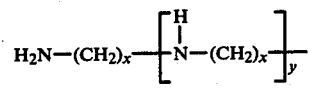

if $R^1$ or $R^2$ or both are

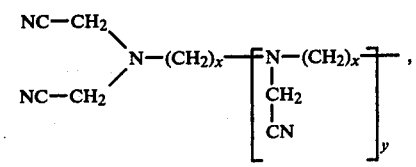

and $R^3$ can also have the same meaning as $R^1$ if $R^1$ is an alkyl of 1 to 8 carbon atoms and x and y have the above meanings, wherein the reaction is conducted at a pH of below 2, and at from 10° to 70° C., and wherein hydrogen cyanide is added to the reaction mixture at a rate such that the concentration of hydrogen cyanide during the reaction is not more than 3 percent by weight, based on the total reaction mixture.

2. A process as set forth in claim 1, wherein the reaction is carried out with from 1 to 1.1 moles of starting material II and/or from 1 to 1.1 moles of hydrogen cyanide per mole of formaldehyde.

3. A process as set forth in claim 1, wherein the reaction is carried out at from 10° to 60° C.

4. A process as set forth in claim 1, wherein the reaction is carried out at from 15° to 55° C.

5. A process as set forth in claim 1, wherein the reaction is carried out at from 20° to 49° C.

6. A process as set forth in claim 1, wherein the reaction is carried out with a total of from 40 to 80 percent by weight, based on formaldehyde, of water.

7. A process as set forth in claim 1, wherein, during the reaction, the concentration of hydrogen cyanide in the reaction mixture is from 0.01 to 3 percent by weight.

8. A process as set forth in claim 1, wherein, during the reaction, the concentration of hydrogen cyanide in the reaction mixture is from 0.01 to 2 percent by weight.

9. A process as set forth in claim 1, wherein, during the reaction, the concentration of hydrogen cyanide in the reaction mixture is from 0.01 to 1 percent by weight.

* * * * *